(12) United States Patent
O'Leary

(10) Patent No.: US 6,926,901 B2
(45) Date of Patent: Aug. 9, 2005

(54) SUBERIZATION OF A POLYMERIC SUSTAIN RELEASE MATRIX FOR ANIMAL REPELLANCY

(75) Inventor: Robert K. O'Leary, Deltaville, VA (US)

(73) Assignee: The Corato Foundation, Deltaville, VA (US)

( * ) Notice: Subject to any disclaimer, the term of this patent is extended or adjusted under 35 U.S.C. 154(b) by 0 days.

(21) Appl. No.: 10/419,882

(22) Filed: Apr. 22, 2003

(65) Prior Publication Data

US 2003/0202998 A1 Oct. 30, 2003

Related U.S. Application Data

(63) Continuation-in-part of application No. 09/735,071, filed on Dec. 12, 2000, now Pat. No. 6,565,867.

(51) Int. Cl.[7] .............................................. A61K 35/78
(52) U.S. Cl. .................... 424/405; 424/418; 424/78.08; 424/725; 424/753
(58) Field of Search ................................ 424/405, 418, 424/417, 407, 725, 195.1, 753, 400, 406, 78.08

(56) References Cited

U.S. PATENT DOCUMENTS

| | | | |
|---|---|---|---|
| 3,940,488 A | 2/1976 | Frohberger et al. | |
| 5,221,535 A | 6/1993 | Domb | |
| 5,290,557 A | 3/1994 | Mason et al. | |
| 5,356,881 A | * 10/1994 | Verbiscar | ..................... 514/26 |
| 5,738,851 A | 4/1998 | Colavito | |
| 6,395,290 B2 | * 5/2002 | Brown | ........................ 424/408 |

OTHER PUBLICATIONS

The Merck Index, 10th Edition, 1983, Merck & Co., Inc., p. 1090.

* cited by examiner

Primary Examiner—Leon B. Lankford, Jr.
Assistant Examiner—Ruth A. Davis
(74) Attorney, Agent, or Firm—Baker & McKenzie LLP

(57) ABSTRACT

The invention is an animal repellant composition containing one or more plant derived toxins, including for example one or more alkaloids isolated from for example, one or more members of the family *Narcissus*, and optionally containing one or more polymers, including for example one or more bioerodible polymers and/or more non-absorbable polymers. The animal repellant composition is useful for repelling animals from vegetation and for rendering vegetation unpalatable to animals. The invention also includes methods for repelling animals, as well as methods for treating vegetation to render the vegetation unpalatable to animals, such animals including for example, deer, voles, moles, ground hogs, mice, rats, rodents, raccoons, nematodes, larvae, worms, fungi, molds, bacteria, vegetative organisms, and insects. A suberin-polymer-repellant chemical complex and a method for treating damaged vegetation are also disclosed.

34 Claims, No Drawings

US 6,926,901 B2

SUBERIZATION OF A POLYMERIC SUSTAIN RELEASE MATRIX FOR ANIMAL REPELLANCY

This application is a continuation-in-part of U.S. patent application Ser. No. 09/735,071, filed Dec., 12, 2000, now U.S. Pat. No. 6,565,867.

FIELD OF THE INVENTION

The invention is directed to animal repellent compositions containing plant derived toxins including for example, alkaloids isolated from botanical specimens of the family Amaryllidaceae including for example from the genus *Narcissus*; and other moieties including for example cycad extracts, useful for repelling unicellular and multicellular animals from materials including vegetation including flowers, plants, vines, food crops, bulbs, seeds, nuts, fruits, bushes and trees. These compositions may optionally include one or more other agents, including for example, bioerodible polymers, biochemicals, and/or permeation enhancers. The compositions can be topically applied to the desired material and/or the desired material can be permeated with the composition. Methods of application include, for example, coating, directly spraying, dip coating, spray coating, painting on, impregnating, soaking, vacuum deposition, or electostatic coating and electrolytic diffusion. The inventive compositions are effective in repelling organisms including animals such as animals that disturb vegetation, for example animals that eat, gnaw, or sense vegetation, e.g., deer, voles, moles, ground hogs, mice, rats, rodents, raccoons, the Amera sub phylum including the class, order and phylum of Mollusca Gastropoda, nematodes, larvae, worms, and insects.

BACKGROUND OF THE INVENTION

Animals are responsible for costly and unsightly damage to vegetation, the vegetation including everything from seeds, crops to the backyard garden. Accordingly, there is a strong need for a composition and method for deterring such animals from disturbing vegetation without causing permanent damage or death to the foraging animal.

SUMMARY OF THE INVENTION

The invention solves the problem of animal destruction of vegetation by providing an animal repellant composition containing one or more plant derived toxins, which composition renders vegetation and/or vegetable matter unpalatable to animals.

The invention is directed to a method for repelling animals from vegetation including treating vegetation, with an animal repellant composition containing one or more plant derived toxins.

The invention is directed to a method for repelling animals from vegetation including treating vegetation, with an animal repellant composition containing one or more alkaloids and/or plant biochemicals extracted from one or more members of family Amaryllidaceae and/or Liliaceae.

The invention is directed to an animal repellant composition containing one or more plant derived toxins.

The invention is directed to an animal repellant composition one or more alkaloids extracted from one or more members of the family Amaryllidaceae and/or Liliaceae.

The invention is directed to a method for repelling animals and a composition for repelling animals, where the alkaloid is isolated from the genus *Narcissus*.

The invention is directed to a method for repelling animals from vegetation, where the bulb is treated with the animal repellant composition by permeating the bulb with the composition.

The invention is directed to a method for repelling animals from vegetation, where permeating is carried out by soaking the bulb in the animal repellant composition.

The invention is directed to an animal repellant composition further containing one or more polymers.

The invention is directed to an animal repellant composition where the polymer is a bioerodible polymer and/or a non-absorbable polymer.

The invention is directed to a method for repelling animals from vegetation, where the animal repellant composition contains one or more polymers.

The invention is directed to a method for repelling animals from vegetation where the polymer is a bioerodible polymer and/or a non-absorbable polymer.

The invention is directed to a method of preventing animals from disturbing planted bulbs including treating the bulbs prior to planting, with an animal repellant composition containing one or more plant derived toxins.

The invention is directed to a method of preventing animals from disturbing planted bulbs including treating the bulbs prior to planting, with an animal repellant composition containing one or more alkaloids extracted from one or more members of the family Amaryllidaceae and/or Liliaceae.

The invention is directed to a method of preventing animals from disturbing planted bulbs including treating the bulbs prior to planting, with an animal repellant composition containing one or more alkaloids extracted from one or more members of the genus *Narcissus*.

The invention is also directed to a method of preventing animals from disturbing planted bulbs where the animal repellant composition further contains one or more polymers, where the polymer is a bioerodible polymer and/or a non-absorbable polymer.

The invention is directed to a method for producing an unpalatable plant bulb including treating one or more plant bulbs with an animal repellant composition including one or more alkaloids extracted from one or more members of the genus *Narcissus*.

The invention is also directed to a method of producing an unpalatable plant bulb including treating one or more plant bulbs with an animal repellant composition including one or more plant derived toxins.

The invention is directed to a method of producing an unpalatable plant bulb including treating one or more plant bulbs with an animal repellant composition including one or more alkaloids extracted from one or more members of the family Amaryllidaceae and/or Liliaceae.

The invention is further directed to a method of producing an unpalatable plant bulb where the animal repellant composition further contains one or more polymers, where the polymer is a bioerodible polymer and/or a non-absorbable polymer.

The invention is also directed to a method of producing an unpalatable plant bulb where the step of treating includes permeating the bulb with the animal repellant composition.

The invention is directed to a method of producing an unpalatable plant bulb where permeating the bulb with the animal repellant composition is carried out by soaking the bulb in the composition.

The invention is directed to a method of producing an unpalatable plant bulb where the step of soaking the bulb in the composition, is carried out in a positive or negative pressure environment.

The invention is further directed to an animal repellant composition containing one or more plant derived toxins, and one or more polymers.

The invention is directed to a treated plant bulb including one or more plant bulbs treated with an animal repellant composition containing one or more alkaloids extracted from one or more members of the genus *Narcissus* under conditions effective to render the treated plant bulbs unpalatable to animals.

The invention is also directed to a treated plant bulb where the animal repellant composition further contains one or more polymers, where the polymer is a bioerodible polymer and/or a non-absorbable polymer.

The invention is directed to composition, bulb or method, where the bioerodible polymer is preferably one or more of polyorthesters, pluronic F-127, carboxymethyl cellulose, lactide-glycolide co-polymers, and methyl cellulose.

The invention is directed to a treated plant bulb where the bulb is treated with the animal repellant composition by permeating the plant bulb with the animal repellant composition.

The invention is directed to a treated plant bulb where the bulb is permeated with the animal repellant composition by soaking the bulb in the composition.

The invention is directed to a treated plant bulb where the bulb is soaked with the animal repellant composition in a positive or negative pressure environment.

The invention is directed to a treated plant bulb where the bulb is treated with the animal repellant composition for an amount of time effective to render the bulb unpalatable to animals.

The invention is also directed to a method for producing an unpalatable plant bulb, including permeating the plant bulb with a first animal repellant composition including one or more plant derived toxins to produce a permeated bulb; drying the permeated bulb to produce a dried bulb; and coating the dried bulb with a second animal repellant composition including one or more plant derived toxins, and one or more polymers.

In another embodiment, the invention is a chemical and physical complexation of repellant moieties to a synthetic high molecular weight polymer which in turn may be bound by secondary chemical forces to the natural suberin polyesterified biopolymer in plant roots and plant cell walls. This interaction forms a macromolecule that contains three spatially distinct structures, which are bound together. This macromolecular Suberin—Synthetic Polymer—Repellant complex acts as an anti-predator, anti-bacteria, anti-fungi, anti-mold, and anti-insect composition when in contact with plant tissue. The composition of the invention also acts as a water retentor and antimicrobial barrier while preventing loss of plant tissue to predation by animals such as moles, voles, rabbits, mice, rats, etc. The complex also provides for mycorrhizal development. Aqueous, alcoholic, surfactant, and organic solutions of the synthetic high molecular weight linker polymer with its bound animal repellant can be applied to seminal roots, adventitious roots, lateral roots, feeder roots, primary roots, secondary roots, and coarse roots which contain suberin biopolymer domains and thus provide the protective activities described above.

In another aspect, a method for protecting vegetation is disclosed wherein the roots of a plant or vegetation are treated with one or more plant-derived, repellant chemicals, and one or more polymers to form a suberin-polymer-repellant complex for repelling animals, bacteria, fungi, mold, insects, and other harmful actors.

In yet another aspect, a method for protecting damaged vegetation containing suberin is disclosed whereby one or more polymers are applied to the damaged area of the vegetation, and a matrix is formed between the one or more polymers and the suberin of the vegetation to protect the vegetation.

DETAILED DESCRIPTION

I. Definitions: The below definitions serve to provide an understanding of the specification and claims, including the scope to be given such terms.

Plant Bulb. By the term "plant bulb" is intended for the purposes of the invention, any subterranean and globular bud having fleshy leaves emergent at the top and a stem reduced to a flat disk; any short, vertical underground stem of plants; including for example, flowering plant bulbs, and plant bulbs including onion and garlic.

Plant Derived Toxin. By the term "plant derived toxin" is intended an active agent derived from one or more plant sources, i.e. one more naturally occurring phytotoxins, and includes alkaloids extracted from plants including plants that are members of the family Amaryllidaceae and/or Liliaceae, including plants belonging to the genus *Narcissus*. Suitable phytotoxins for use in the invention include but are not limited to: hormones, neurotransmitters, caffeine, saponins, tomatine, alkaloids, taxine, ranunculin, buxene, conine, strychnine, cardiac glycosides, nerioside, oleandroside, convallarin, digitoxin, prunasin, amygdalin, ricin, lectin, wistarine, tryamine, phoratoxin, viscotoxin phytolaccigenin, phytolaccatoxin, oxalic acid, oxalates, solanine, tannins, urushiol oil, steroidal alkaloids, rotenone, pyrethrum, oubane, abrin, polypeptides, amines, resins, toxalbumins, aglycones, indole alkaloids, beta carbolines, indolizidine, piperidine, polycyclic diterpene, pyrrolizidine, quinolizidine, tropane, typtamine, nitrates, nitrites, phytates, mycotozins, phenolics, toxicants, metals, heavy metals, lipids, erucic acid, fluoracetate, glycolipids, abris, concanacalin, robin, mimosine, sesquiterpene, lactones, lathyrogens, canavanine indospecine, plant carcinogens, alsike, ipomemaron, aconitine, narcotic alkaloids, aconitine, saportins, aethusin, cicutoxin, barbaloin, lycorine, protoanemonin, protopine, berberine, sanguinarine, dihydroxysanguinarine, isothiocyanate, betaphenyl isothiocyanate, aucubim, protoanemonin, n-methylcytisine, nicotine, conime, oil of croton, cycasin, macrozainin, mezereinic acid anhydride, atropine, hyoscyamine, scopolamine, protopine, isoquinoline alkaloid, tremetol, phorbol esters, gelsemine, gel eminine alkaloids, colchicine, hederagenin, hederin, tremetol, isisen, toxalbumin curcin, juglone, andromedotoxin, cytisine, lantanin, lobeline, mescaline, lupinone, cyanogenic compounds, amygdalin, grayanotoxin, allicin, propanethial s-oxide, spices, eugenol, isoeugenol, safrole, myristicin, elemicin, limolene, linamarin, aflatoxins, goitrogens, canavanine, coprine, anersine, carnosine, viscotoxins, and disulfiram.

*Narcissus*. By the term "*Narcissus*" is intended for the purposes of the invention, any bulbous plant belonging to the genus *Narcissus*, of the amaryllis family.

Alkaloid. By the term "alkaloid" is intended for the purposes of the invention, a basic nitrogenous organic compound of vegetable origin which is biologically active and has toxic potential, usually derived from the nitrogen ring compounds and isolated from for example, one or more members of the family Amaryllidaceae, such members including for example, *Narcissus, Galanthus, Amaryllis Belladonna, Childanthus Fragrans, Crinium x Powellii,*

*Cyrthanthus Elatus, Scadoxus, Sprekelia Formosissima, Leucojum, Nerine Bowdenii, Nerine sarniensis, Sternbergia, Eucharis Amazonica, Hippeastrum, Hymenocallis, Zephyranthus, Pamianthe Peruviana, Phaedranassa Carmioli,* and *Habranthus,* more preferably *Narcissus,* and *Galanthus,* and most preferably *Narcissus*; and one or more members of the Palm family including Cycads.

Permeate. By the term "permeate" is intended for the purposes of the invention, the act of diffusing, sorbing, or permeating a substance with another substance, per the Fickian law of Diffusion.

Polymer. By the term "polymer" is intended any polymers and coatings including but not limited to bioerodible polymers, absorbable polymers, non-absorbable polymers, human fibrogen, and cactus sap. Suitable absorbable polymers include but are not limited to DL-lactide-co-glycolide; L-lactic acid; DL-α-hydroxy-n-butyric acid; DL-α-hydroxyisocaproic acid; poly propylfumarate-methyl methacrylate; poly methyl methacrylate; polyhydroxyethl-L-glutamine; polyiminocarbonate; poly (α-hydroxy acids); polyglecaprone 25; polyglyconate; polyglycolide; poly (ether urethane urea); Atrigel (Atrix Laboratories, Fort Collins, Colo.; Atrigel RG502H is 50/50 poly DL lactide co-glycolide); polyphosphate; polyphosphonate; polyphosphite; fibrin adhesives; polyphosphoesters; polyethylene terephthalate; poly(anhydrides); poly (ester-anhydrides); poly (anhydride)-co-imides; polyorthoesters; polyphosphozenes; poly lactic acid; poly glycolic acid; polyvinyl alcohol; precipitated protein; polymethyl methacrylate; collagen; fibrinopeptides; poly-p-dioxanone; gelatin; and cross-linked collagen. Suitable controlled release polymers include but are not limited to: polysaacharides; glycones; fructose; cactus sap; plant saps; chitosans; cellulosics; deacetylated cellulose acetate; collodion; plaster of paris; poly (propylenefumarate)methyl methacrylate; polytetrafluoroethylene; polyurethane; poly vinyl alcohol; polystyrene; polyolefin; poly vinyl polymer; 1,3,5 ,-benzene tricarboxylic acid branched polymers; n-alkyl-2-cyanoacrylates including methyl, butyl, octyl and hexyl; carboxy methyl cellulose; methyl cellulose; demineralized xenogenic bone matrix; poly caprolactone; isoplithalic acid-sebacic acid copolymers; pluronic; polyesters; polyglyconate; poly (α-esters); poly dimethyl siloxane; polyglcolide; polylactide; copolymers of poly (lactide-co-glycolide); biodegradable ceramics; carboxyphenoxyvalerate polymers; and bis(2-hydroxyethyl)terephthalate.

Bioerodible Polymer. By the term "bioerodible polymers" is intended for the purposes of the invention, bioerodible, bioresorbable, bioabsorbable, and biodegradable materials that are well known in art and are described in *Biomaterials Science-An Introduction to Materials in Medicine,* edited by Ratner, B. D. et al., Academic Press, (1996), and include for example, the following materials: chitosan; isomorphic poly(hexamethylene co-trans-1,4-cyclohexane dimethylene oxalates); poly(glycolic acid); copolymers of poly(glycolic acid) and poly(lactic acid); polydioxanone; poly(lactic acid); polymers having a back-bone structure selected form the group consisting of polyanhydrides, polyphosphazenes, polyphosphonates, polyamides, and polyimino carbonates; polyhydroxybutyrate; polyhydroxyvalerate; copolymers of polyhydroxybutyrate and polyhydroxyvalerate; polycaprolactone; polydioxanone; poly (γ-ethyl glutamate); poly(DTH iminocarbonate); poly(Bisphenol A iminocarbonate); poly(DETOSU-1,6 HD-t-CDM ortho ester); poly(Sebacic acid-hexadecandioic acid anhydride); poly(ortho esters); poly(amino acids); Pluronic F-127 and PLOA.

Non-absorbable polmer. By the term "non-absorbable polymer" is intended all polymers that are not resorbable, bioerodible, or biodegradable. Suitable polymers for use in the invention, include: polytrifluorochloroethylene; olyvinyl pyrrolidone; polymethacrylamide; polyethylene terphthalate; rubber; styrene acrylonitrile; polyvinylidenechloride; polyvinyl alcohol; polyvinyl acetate; polymethyl methacrylate; nylon 6,6; nylon 6; polyvinylchloride; polyethylene; polyurethane; polytetrafluoroethylene; polypropylene; polystyrene; polyvinylidene fluoride; polybutadiene; polyisobutene; polyethylene oxide; natural cellulose; epoxy resin; polyisoprene; cellulose triacetate; methyl cellulose; methyl silicone rubber; dimethyl siloxane; polyphenylene oxide; polypeptide; polysulfone; polypropylene glycol; polysorbate; polyesters; polyethers; polyglycols; polyimides; polycarbonates; polybutylene; polyacrylates; polyamide; polybutene; and polyvinyl carbazole.

Animal. By the term "animal" is intended for the purposes of the invention, any unicellular or multicellular organism including any member of the kingdom Animalia, including for example, deer, voles, moles, ground hogs, mice, rats, rodents, racoon, nematodes, larvae, worms, and insects; and unicellular animals including for example bacteria fungus, molds, and others which destroy vegetation including seeds and bulbs.

Vegetation. By the term "vegetation" is intended for the purposes of the invention, all plants or plant life; by the term "plant" is intended for the purposes of the invention, any member of the kingdom Plantae, including at any and all stages of growth and development.

Seed. By the term "seed" is intended for the purposes of the invention, any small part or fruit of a plant, including for example, any propagative part of a plant.

Solvent. Suitable solvents for use in the extraction process include but are not limited to water, ethanol, and other organic hydrocarbon molecules including for example, chloroform, alcohols, ketones, benzenes, carboxylic acids, glycols, ethers, esters, N-methyl-2-pyrrolidone, and/or diethyl ether.

Permeation Enhancer. Suitable permeation enhancers include surfactants, detergents, and solubilizers, including for example but not limited to: Nonidet P-40, Triton X-100, and Non-oxynol 9, such permeation enhancers may optionally be added to the extracting solvent to for example, accelerate the leaching of the active alkaloid factor. Permeation may also be varied by varying other parameters including temperature, agitation, radiation, pressure, surface area and particle size. For example, an increase in temperature, agitation, or pressure will result in greater permeation of the material being treated with the inventive composition.

Suberin. By the term "suberin" is intended any of the long chain fatty acid polyesterified polymers contained in terrestrial, vascular, eukaryotic, photosynthetic, multicellular, sexually reproducing plants. Suberin is present in the thickened cell walls of trees and shrubs, such as in the corky tissues. In particular, as an example, it is found in green cotton fibers, potatoe tubers, maize, birch bark, douglas fir bark and peach bark, and generally in the cortex of plant root walls and the peridermis and exodermis of higher plants.

II. Method of Making the Animal Repellant Composition

Plant toxins including but not limited to alkaloids contained in plant material, for example plant bulbs including but not limited to *Narcissus* bulbs, are not easily separated from the bulb fiber and mucilaginous substances. Thus it is preferable to use dry plant material or bulbs or plant material or bulbs frozen in liquid carbon dioxide or liquid nitrogen, since it allows grinding to be carried out with greater efficacy. The increased surface area of the ground material improves the rate of extraction of the alkaloids. By using a temperature of about 100° F., the reaction rate for extraction doubles for every rise of ten degrees over ambient temperature.

A. Extraction of Alkaloid

The alkaloids can be extracted by any means know in the art. Suitable extraction methods are set forth below.

(1) The biological active alkaloid is extracted from the plant material for example one or members of the family Amarylidaceae, preferably *Narcissus*, by first cleaning the plant to be subject to extraction; and cutting up the cleaned plant material into small pieces. The cut plant material is then allowed to dry. Drying can be carried out naturally, for example, at room temperature, or in the sun, or can be carried out for example in a low-temperature drier, a vacuum evaporator, or an oven. The dried, cut, plant material is then ground into a powder. The plant powder may then be subject to extraction or stored for extraction at a later date.

The powder plant material is then extracted, for example in a percolator, with warm to hot acidulated alcohol, suitable acids including, for example, acetic acid, citric acid, 1-malic acid, tartaric acid, oxalic acid, sorbic acid, benzoic acid, D-malic acid, phosphoric acid, lactic acid, cotratic acid, ascorbic acid, fumaric acid, boric acid, gluconic acid, and maleic acid, at a temperature of from about 5° C. to about 50° C., the acid at a concentration of from about 0.05% to about 7%, preferably 0.1% to about 5.0%, more preferably 0.2% to about 4.0%, and most preferably about 0.3%. Suitable alcohols including for example ethanol at a concentration of from about 75.0% to about 100.0%, prefereably from about 85.0% to about 98.0%, and most preferably about 96.0%.

The extract is then filtered and concentrated. Water is then added to the concentrate and the solution is concentrated again. The second concentrated solution is thereafter filtered to separate oils, resins, chlorophyll, etc., and the filtered materials are then washed twice with an organic solvent. Suitable solvents include, for example, chloroform, ethanol, and ehters. The aqueous washed solution is then neutralized with, for example, solid potassium carbonate, and an excess of the neutralizing compound is added. A precipitate containing only the neutralizing compound is eliminated, and the solution is extracted four times with a like volume of solvent, for example, chloroform.

The combined solvent extracts, after having been dried with anhydrous sodium sulfate are concentrated and filtered. The solution is extracted twice with a dilute aqueous acid, for example, 3.0% hydrochloric acid, and once with water. The aqueous solution is washed with an organic solvent, including for example ether and/or ethanol, repeatedly and filtered. The remaining aqueous solution is the purified aqueous solution of total alkaloids.

The total alkaloids may be further purified by first alkalinized again with, for example, dry potassium carbonate, and extracted multiple times, for example, about five times, with an organic solvent for example ether. This extract containing the ether soluble alkaloids, is then concentrated and this is concentrate A.

The basic aqueous solution is then extracted about three times with an organic solvent for example chloroform, and the extract is then concentrated and this is solution B.

Solution B is then extracted twice with an acid, for example hydrochloric acid at a concentration of about 1.0% to about 10.0%, and preferably at about 5.0%, and is extracted once with water. The aqueous extract is then washed with, for example, chloroform/ether. After alkalinization with potassium carbonate, the solution is again extracted with, for example, chloroform and the chloroform extract evaporated to dryness. After neutralization with alcoholic hydrochloric acid, the crude hydrochloride is then dissolved in alcohol, for example absolute ethyl alcohol, and then the filtered solution is overlaid with ether.

(2) Another extraction method is as follows: The biological active alkaloid is extracted from one or members of the family Amaryllidaceae, preferably *Narcissus*, by first cleaning the plant to be subject to extraction, and then cutting up the cleaned plant material into small pieces. The cut plant material is then mixed with a solvent with agitation until thoroughly mixed. Preferably, the agitation is continued for at least one minute. Suitable solvents include water, organic solvents including, for example, ether and chloroform, and other solvents provided the active alkaloid is soluble in the solvent and the solvent is non-toxic to the vegetation to which the composition is to be applied.

(3) The preferred extraction method is as follows: The biological active alkaloids are extracted from one or members of the family Amaryllidaceae, preferably *Narcissus*, by the first cleaning the plant, preferably plant bulbs, to be subject to extraction; optionally allowing the plant material to dry or drying the plant material; and then finely cutting up the cleaned plant material into very fine pieces, using, for example, a food processor. Thereafter, the chopped plant material is added to alcohol, for example alcohol USP, binary azeotrope (binary azeotropic mixture is a mixture of alcohol and water including for example 70% alcohol and 30% water) preferably containing a surfactant for example nonoxynol-9, and dry acid, for example, dry citric acid monohydrate, in a ratio of about 1000 ml alcohol to about 5 ml surfactant to about 30 g dry acid. Suitable alcohols include methanol, ethanol, propanol and iso-propyl alcohol. Suitable surfactants include detergents including anionic and nonionic detergents, wetting agents, emulsifiers including soaps, and any compound that reduces the surface tension when dissolved in water or water solutions, or which reduces interfacial tension between two liquids, or a liquid and a solid, and include for example: Tween 80, Igepol CO-630, Triton X-100, NONIDET P-40, and Non-Oxynol 9. Suitable acids include: 1-malic acid, tartaric acid, oxalic acid, sorbic acid, acetic acid, citric acid, benzoic acid, DL-malic acid phosphoric acid, lactic acid, cotratic acid, ascorbic acid, fumaric acid, boric acid, gluconic acid and maleic acid. The solution and plant material are then vigorously and continuously stirred for a period of time of from about 6 hours to about 20 hours, preferably from about 8 hours to about 16 hours, and more preferably for about 12 hours, at a temperature of from about 80° F. to about 120° F., preferably about 100° F. Thereafter, the alcohol/surfactant/acid supernatant solution is passed through a sieve, for example a 500 $\mu$m sieve (USA standard testing sieve no: 35) and the sieved solution is allowed to cool to ambient temperature. This extract solution contains the alkaloids.

The *Narcissus* bulb is preferably exhaustively extracted in hot, acidulated ethanol (3% citric acid in 190 proof ethanol alcohol US containing surfactant). Suitable acids, alcohols, and surfactants are as listed above. The alkaloid is soluble in the ethanol and the plant protein is swollen by the citric acid's hydrogen ion concentration. The citric acid is also used as a antioxidant protectant, a preservative, and as an anti-micorbial agent for the extracted bulb when placed in the ground. The citric acid is a physiological, non-toxic, tissue metabolite and, as such, does not have to be neutralized with potassium carbonate or other suitable buffer. The citrated salt can be purified and concentrated to dryness in order to characterize it with a pure melting point, but is not necessary for the active alkaloid to be transferred from one plant tissue to another. The extracting ethanol solvent can be replaced with other organic hydrocarbon molecules including for example, chloroform, alcohols, ketones, benzenes, carboxylic acids, glycols, ethers, and/or diethyl ether. The permeation of the ethanol is accelerated by the use of surfactants/solubilizers/detergents, including for example Nonidet P-40, Triton X-100, Tween 80, IGEPOL CO-630, and Non-oxynol 9, and the leaching of the active alkaloid factor is also accelerated by these same permeation enhancers.

The rate of extraction and the transfer of the active alkaloid factor, using any extraction method, can be accelerated by carrying out these procedures in an ultrasonic bath operated at a range of from about 40 KHz to about 47 KHz for time pulses of from about 10 min. to 20 min., preferably about 15 min. each, without adverse physical and chemical effects on the treated bulb or on the extracted alkaloids.

B. The Inventive Composition

The alkaloid containing extract can be used as is or can be combined with one or more factors, such factors including for example one or more of: a bioerodible polymer; a diffusion matrice including for example egg albumin; cubic crystalline phases of monoolein, water and lecithin; a polyorthoester; a non-absorbable suture material; collagen; and other materials including proteins that are capable of functioning as a release matrix for the active alkaloid; and other materials having a high degree of adhesion to the plant material (i.e. a bulb surface). Other suitable additives which may optionally be included, include: insecticides; rooting hormones; primary nutrients for plant growth including nitrogen sources including, for example, urea, ammonium nitrate, and ammonia, phosphorus from for example super phosphates, and potassium for example potassium chloride; secondary nutrients including calcium, magnesium, and sulfur, trace element including iron, copper, boron, manganese, zinc, molybdenum. The foregoing primary and secondary nutrients can be added as is or can be added to the inventive composition in a controlled release form for example, by coating the nutrients with polymeric sulfur, and by, for example, polymeric micro encapsulation of the nutrients. The advantage to a controlled release form is that the nutrients are released at a uniform rate. Other suitable additives which may optionally be included in the composition include for example one or more of an anti-fungal, a fertilizer, a plant growth enhancer, antioxidant protectant, a preservative, an anti-microbial agent, and a soil enhancer.

The composition preferably contains the alkaloid extract and at least one or more bioerodible polymers. The alkaloid extract is preferably added to the polymer solution to form the composition. Other factors may be added to the polymer solution, the extract, or the polymer/extract composition.

Another composition of the invention includes a macromolecular Suberin-Synthetic Polymer-Repellant complex. Suberin, which is contained in terrestrial, vascular, eukaryotic, photosynthetic, multicellular, and sexually reproducing plants as long chain fatty acid polyesterified polymers. Typically, the roots of such plants contain 40 wt % suberin, 22 wt % lignin and 9 wt % cellulose and hemicellulose, with the balance water. Each plant root cell in the exodermal and endodermal layer of the basal root zones may bear a defense-related band of waxy suberin. In this embodiment, suberin includes a complex, random network and macromolecular structure of hydrophobic lipid based polyphenolic and polyaliphatic domains in plant endodermal and rhizodermal radial cell walls, which prevents interstitial entry of water into absorbing roots. The attachment of suberin to the cellulosic plant tissue may be enhanced by crosslinking molecules, such as glycerol and caffeoyl residues from cinnamic acids.

Suberin is perhaps best known as the chemical that produces human tears upon peeling an onion. This suberin barrier or suberization process may include a response to injury or pathogen invasion. The hydrophobic tissue layer may also bind and attach to synthetic, high molecular weight, macromolecular long-chain polymers (thermosetting, thermoplastic, elastomeric) such as, hydroxyethyl methacrylate, hydroxy methyl cellulose, hydroxypropyl methyl cellulose, hydroxypropylcellulose, carboxy methyl cellulose, methyl cellulose, alpha-cellulose and other water soluble polymers, such as polyethylene oxide, polyethylene glycols, polymeric micelles, N-(2-hyroxypropyl) methacrylamide, polyvinyl alcohol, polyacrylic acid, pectin, agar, chitin, alginates, starch, dextrins, algin, dextrose, albumen, corn zein, dendrimers, soy protein isolate, collagen, whey, glycerolized demineralized bone, gellan gum, food grade shellac, polyvinyl pyrrolidone, hydrogels, polyethyl oxazaline, ethylene vinyl acetate. A combination of different polymers and/or copolymers and mixed ligands may be employed. A binding ligand composition may be employed depending on the particular suberin-lignin lipid to be interacted. In general, in a preferred embodiment, the ligand should be substantially hydrophobic, capable of attracting and bonding, by secondary chemical forces, via Van der Waal's forces or hydrophobic forces, to the suberin and lignin to be interacted and capable of being bonded to the polymer through biologically stable ether/ester groups.

The macromolecules of the invention may be found mixed, attached, and bound to small molecules such as lipids, alkaloids, animal repellants, surfactants, plasticizers, at interfaces, such as suberin Casparian Strips and synthetic high molecular weight polymers. For example, in the context of animal repellant complexes, the lipid composition, structure and polymer physicochemical properties influence the polymer-lipid interaction and the thermodynamics and kinetics of animal repellant diffusion into the plant root from the biopolymer system. The behavior of the biopolymer system is strongly dependent on the differences in plant lipid structure and the ability of the linker polymer carrier/adherent and the lipid suberin polymer to interact with one another.

In one aspect of a Suberin-Linker Polymer Carrier/Adherent-Animal Repellant System, the interaction comes in the form of hydrogen bonding between the lipid hydroxyl groups and the ester groups in the selected linker polymer. Polymers that form films may be composed of carbohydrates, protein, solid lipid/wax, or resin. These linker polymers may be the adherent vehicle, the polymer-lipid interactor, and sustain release carriers of the animal repellants, such as secondary plant metabolites such as strychnine, morphine, codeine, atropine, vincristine, quinine, caffeine, nicotine, alkaloids, menthol and other known compounds which are described above.

The hydrophobic, lyophilic suberin located in the plant root periderm/endodermis-selective membrane is composed of cells which have a band of suberin, which is mostly gamma hydroxy acids—called a Casparian Strip—embedded in the plant endodermal cell wall, which prevents the entry of interstitial water into the stele. By way of this strip, linker polymers may become bound to the root. In one aspect of the invention, the carrier-adherent linker polymer is attached to animal repellant molecules, such as alkaloids. In one aspect the hydrophobic, lyophilic suberin co-polymer domains may be an interpenetrating polymer matrix with the synthetic linker polymer and the animal repellant moiety. In a preferred embodiment, suberin, the linker polymer, and the animal repellant may swell or expand into one another to form a cohesive bond. In another embodiment, bonding occurs without dissolving the suberin, polymer, or repellant.

This interfacial interaction and intermolecular association may influence the physiochemical properties of the suberin-polymer linkage. The hydrophobic fatty acid domain may co-exist with the hydrophilic domain ends and may lead to a condensation reaction between the hydrophilic glycerol hydroxyl group molecules and the fatty acid, which may result in an ester linkage (mono, di, tri glycerides) in the suberin-polymer-repellant. The rough, high root surface area may have a beneficial effect on the adhesion of the linker polymer to the root. In a preferred embodiment, the macroporous, high-adhesion, polymer surfaces readily form the sustain release complex, which delivers repellant material to the roots of a plant, thus preventing damage and providing the plant root with protection against attack, insect invasion, infection by bacterial and fungal spores, dehydration, etc.

Suberin is an important wound-repair substance in plant root hairs. A protective coating and a polymeric long chain mixture of fatty acids, hydroxylated fatty acids, and long chain alcohols and phenolics such as suberin may be spontaneously generated within 48 hours after the wounding of a plant root.

The wound-healing components of suberin, polyphenolic and polyaliphatic domain compounds, are linked through ester bonds and may covalently bond, hydrogen bond, and ionically bond to synthetic linker absorbable and non-absorbable polymer carriers and adherents containing animal repellant agents in a dynamic state of bond equilibrium in a matrix or complex. It is believed that the strongest intermolecular bonding forces of suberin to a linker polymer are covalent bonds, followed by ionic bonds, dipole-dipole interactions, electrostatic interactions, coordination complexation dispersion forces, Van der Waals forces, and second hydrogen bonding.

As discussed above, suberin is readily esterified/crosslinked with glycerol resulting in suberin triglyceride regions or fatty regions. The linker synthetic polymers are analogous to long chains that form a complex tangled network such as a stack of chains folded back on themselves that give rise to amorphous disordered regions in the polymer. Such amorphous regions permit the diffusion of smaller molecules like glycerides and glycerol found in suberin. The regions may also permit the incorporation of the animal repellant molecules, which is known as intentional and unintentional external plasticization and sorption/diffusion into the amorphous zones of the linker polymer. In a preferred embodiment, the plasticized surface of linker polymers may permit the buildup of inter and intra molecular forces of attraction between the suberin polymer and the sustain-release repellant synthetic polymer carrier.

The most prominent chain lengths in the Casparian Strips, discussed above, are C(16) and C(18) which provide excellent covalent binding sites for the linker polymer/animal repellant matrix. Higher suberin chain lengths of C(24) and C(26) have been reported in the literature. It is believed that suberin compositions rarely change with increasing age. The suberin of the plant roots Casparian Strips contain high amounts of carboxylic and 2-hydroxy acids which provide bonding sites for the linker polymer matrix. Suberin may be mixed with other plant root lipids to form a wax which in turn may crosslink with available secondary hydroxyl bonds with the linker polymer matrix via covalent, ionic and hydrogen bonding.

Mono, di, tri and polyester-plant-compatible plasticizers in combination with a linker polymer matrix may increase the diffusion of an animal repellant from the linker synthetic polymer. Plasticizing agents may also improve the solubilization of the wax-like nature of the suberin and assist in the bonding of the linker polymer and the endodermal/rhizodermal layers in the plant root. The diffusion coefficient, permeability, solubility, desorption-sorption of the animal repellant molecular concentration in the linker polymer, as well as the repellant's transfer to the suberin layer, may be greatly enhanced by plasticization.

III. Method of Using the Animal Repellant Composition

The plant material to be treated, i.e. bulbs, may be treated with the extract composition, or the extract/polymer composition. The compositions may be applied to the plant material in any manner including for example topical application and/or the plant material can be impregnated with the composition. Methods of application include, for example, coating, directly spraying, dip coating, spray coating, painting on, impregnating, soaking, vacuum deposition, or electrostatic coating.

Preferably, when the extract composition is applied to for example, a bulb, the bulb is soaked in the extract composition for a period of time effective to render the bulb unpalatable to animals, preferably for about 2 hours to about 24 hours, more preferably for about 6 hours to about 20 hours, even more preferably for about 8 hours to about 18 hours, still more preferably from about 10 hours to about 16 hours, and most preferably for about 12 hours, at a temperature of from about 55° F. to about 140° F., preferably from about 85° F. to about 110° F., and most preferably about 100° F., preferably with stirring. The bulbs are then removed from the extract composition and dried, for example allowed to air dry at for example ambient temperature until dry, preferably from about 12 hours to about 48 hours, preferably 18 hours to about 42 hours, and most preferably for about 24 hours. Drying may also be carried out using methods known in the art including drying using heat, for example in an oven, vacuum evaporation, adsorption deliquidification, liquid liquid extraction, dry gas flow exposure, ambient air drying, high speed air/gas flow, freeze drying, centrifugation, distillation drying, and air conditioning. The dried treated bulbs may then be planted.

When the polymer/extract composition is applied to for example, a bulb, the bulb is preferably dip coated in the polymer/extract composition and dried, for example allowed to air dry at for example ambient temperature until dry, preferably from about 12 hours to about 48 hours, preferably 18 hours to about 42 hours, and most preferably for about 24 hours. Drying may also be carried out using methods known in the art including drying using heat, for example in an oven, vacuum evaporation, adsorption deliquidification, liquid liquid extraction, dry gas flow exposure, ambient air drying, high speed air/gas flow, freeze drying, centrifugation, distillation drying, and air conditioning. The dried treated bulbs may then be planted. When heat is used to dry the coated bulb, the heat is preferably mild, for example at temperatures up to an including 60° C., and more preferably at temperatures up to and including 50° C.

Alternatively, a bulb may be soaked in the extract composition as described above. The soaked bulb may optionally be dried as described above. Thereafter, the polymer/extract composition, or a polymer composition not containing the alkaloid extract, may be applied to the bulb, for example by dip coating. The soaked and coated bulb is then dried as described above.

EXAMPLES

I. Making the Animal Repellant Composition

A. Extract Composition: Five *Narcissus* bulbs were finely chopped in a cuisinart mini-prep food processor so as to increase the extracting surface area of the bulbs. The chopped bulbs were then added to a 4 liter erlenmeyer flask containing 1000 ml of 190 proof ethyl alcohol, 5 ml of IGEPAL CA 630 (Nonoxynol-9-surfactant) and 30 g of dry citric acid monohydrate. The solution and bulb chips were vigorously and continuously stirred with a magnetic stirrer for twelve hours at 100° F. At the end of the extraction, the alcohol/surfactant/acid supernatant solution was passed through a 500 $\mu$l sieve (USA standard testing sieve no: 35) and the solution was allowed to cool to ambient temperature. The chopped extracted bulb material was discarded while the extract solution was used as the extract composition.

B. Polymer/Extract Composition: The sodium salt of carboxymethylcellulose (CMC) is a high polymer. 2 grams of medium viscosity CMC were added to 100 ml of U.S.P. grade water, to form a thick, viscous, clear liquid into which the extract composition (i.e. the extracted alkaloids) was then added at a 50:50 vol/vol ratio. The extract composition mixed homogeneously with the polymer. Bulbs were then dip coated into the viscous polymer/extract composition, removed, and allowed to air dry for about 24 hours. The dried polymer/extract composition remained on the surface of the dehydrated or extract composition soaked bulb. The extracted alkaloids have limited water solubility and therefore do not readily leach beyond the immediate vicinity of the planted treated bulb. This limited diffusion pattern along with the alkaloid's toxicity and bitter taste is the mechanism of action for the polymer/extract coated or extract composition soaked and polymer/extract or polymer composition dip coated bulb.

Another suitable polymer used in the polymer/extract or polymer composition, is the block co-polymer manufactured by BASF, Inc. called Pluronic F-127. 40 ml of U.S.P. water was added to 20 g of Pluronic F-127 (dry powder at 32° F., to form a thick, clear to white, liquid into which the extract composition was added (a 50:50 vol/vol ratio). The dehydrated bulb or extract composition soaked bulb (dried or not) was then dip coated with the polymer/extract composition and then warmed at ambient temperature to room temperature. As the polymer/extract composition coated on the bulb reaches room temperature it begins to solidify on the bulb. The active alkaloid is active at the surface of the bulb. The high molecular weight F-127 polymer remains on the bulb for years and soil moisture releases the active alkaloid into the local vicinity thus creating an animal barrier which protects the bulb from being gnawed or consumed.

II. Treating Plant Bulbs with the Animal Repellant Composition

Test Samples:

A. Fifteen *Crocus* bulbs (AC) and five tulip bulbs (AT) were placed in the extract composition of example I, for twelve hours at 100° F. with gentle magnetic bar stirring and the soaked bulbs were then removed and allowed to air dry at ambient temperature for twenty-four hours.

B. Fifteen untreated dehydrated *Crocus* bulbs (BC) (purple flower record) and five Tulip bulbs (BT) (not soaked in the extract composition for twelve hours) were coated and treated. The *Crocus* bulbs (BC) were dip coated and dried with only a CMC polymer solution as described in Example I not containing the extract composition and allowed to air dry at ambient temperature for twenty-four hours. The Tulip bulbs (BT) were dip coated in the polymer/extract solution as described in example I and allowed to air dry at ambient temperature for twenty-four hours.

C. Fifteen *Crocus* bulbs (CC) (white Jeanne d'Arc) and five Tulip bulbs (CT) were dip coated with the Pluronic F-127 polymer/extract solution of Example I, and allowed to air dry at ambient temperature for twenty-four hours.

Control Samples:

D. Fifteen untreated dehydrated *Crocus* bulbs (DC) (white Jeanne d'Arc) and five Tulip bulbs (DT).

E. Fifteen dehydrated *Crocus bulbs* (EC) (purple flower record) and five tulip bulbs (ET) were soaked for twelve hours in the extracting media of Example I containing ethanol, citric acid and surfactant; and air dried at ambient temperature for twenty-four hours.

F. Seven *crocus* bulbs (FC) (mixed species) were dip coated with CMC only; and eight *Crocus bulbs* (FCP) were dip coated with pluronic F-127 only, and were air dried at ambient temperature for twenty-four hours.

(The pure polymer coatings on the *crocus* control samples eliminates the requirement for a pure polymer coating control sample on the tulips. Thus the number of test groups in the tulips is five instead of the seven used for the *crocus*.)

III. Animal Repelling Effectiveness: a Comparison Between Treated and Untreated Plant Bulbs A. Bulb Materials
1. Holland Spring Flowering *Crocus venus* and *Crocus chryanthus* Species-Jeanne d'Arc, Flower Record and mixed colors.
2. Holland Darwin Hybrids Tulipa; Golden Apeldoorn (yellow)-mid spring/largest of the tulips—11 to 12 cm.
3. English Trumpet *Narcissus* cultivated hybrid 12–14 cm yellow trumpet daffodil.

B. Experimental Method

The bulbs from the control and test groups of Example II, were planted at an appropriate depth at the appropriate time of year in each of a control plot and a test plot, each plot having well drained soil where animal infestation had been proven to exist and had been an ongoing problem. The bulbs were planted in soil at below 60° F. The *crocus* bulbs were planted at a depth of two inches and the tulip bulbs were planted at a depth of six inches. The test plot and control plot were suitably marked and observed on weekly basis for signs of animal activity until the *crocus* and/or tulips emerged in March/April. The test plot and control plot containing the planted bulbs was kept moist during the test period.

C. Results

| Bulb Group | #Bulbs planted | #Bulbs consumed | #Bulbs remaining |
| --- | --- | --- | --- |
| DT | 5 | 5 | 0 |
| DC | 15 | 5 | 0 |
| ET | 5 | 5 | 0 |
| EC | 15 | 15 | 0 |
| AT | 5 | 5 | 0 |
| AC | 15 | 15 | 0 |
| FC | 7 | 7 | 0 |
| FCP | 8 | 8 | 0 |
| BT | 5 | 5 | 0 |
| BC | 15 | 0 | 15 |

-continued

| Bulb Group | #Bulbs planted | #Bulbs consumed | #Bulbs remaining |
|---|---|---|---|
| CT | 5 | 0 | 5 |
| CC | 15 | 0 | 15 |

As can be seen from the data, all of the control bulbs, i.e. those bulbs including: untreated (DT), (DC); extracting solution only (ET), (EC); CMC only (FC); and F-127 only (FCP); were all consumed by animals, with no bulbs remaining and growing.

Alternatively, out of the bulbs treated with the animal repellant composition containing polymer and the alkaloid extract, i.e. those bulbs including: CMC and alkaloid (BT) (BC); and F-127 and alkaloid (CT) (CC), of those bulbs planted 87.5% of the bulbs remained, emerged and grew, while only 12.5% of the bulbs were consumed; thus proving that the inventive animal repellant composition is effective for repelling animals from plant bulbs, rendering treated plant bulbs unpalatable to animals, and for treating plant bulbs, without any adverse effect on the plant bulb itself.

The bulbs of the remaining test groups (AT) and (AC), treated with the composition containing the alkaloid and the extracting solution, and no polymer, were all consumed with no bulbs remaining.

The composition of the invention may also used to treat the grasses that are damaged by Canadian Geese, for example. The repellant chemical in combination with polymers and suberin protects the grass from the geese without damaging the grass or its root system.

In another aspect according to the invention, a method for protecting damaged vegetation containing suberin may be employed. One or more polymers may be applied to the damaged area of the vegetation to form a matrix between the polymers and the suberin of the vegetation. Because the matrix acts as a sealant and prevents water loss and rotting, the vegetation is protected at the damaged location. For example, one or more polymers may be applied to the stem of a cut rose to form a suberin-polymer complex. The complex protects the plant from further damage and facilitates the plant's ability to protect and repair itself.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Any references including patents cited herein are incorporated herein in their entirety.

I claim:

1. A combination comprising:
a plant seed containing suberin; and
a biopolymer system for treating seeds containing suberin, comprising:
one or more plant-derived, repellant chemicals; and
one or more polymers, the polymers forming a matrix with the suberin and the plant-derived, repellant chemicals to permit sustained release of the chemicals.

2. The combination of claim 1, wherein the one or more polymers are bioerodible polymers.

3. The combination of claim 1, wherein the one or more polymers are absorbable polymers.

4. The combination of claim 1, wherein the one or more polymers are controlled release polymers.

5. The combination of claim 1, wherein the one or more polymers are one or more high molecular weight, hydrophilic polymers.

6. The combination of claim 1, wherein the one or more polymers are one or more high molecular weight, resorbable polymers.

7. The combination of claim 1, wherein the one or more polymers are one or more hydrolytically and enzymatically degradable polymers.

8. The combination of claim 1, wherein the one or more polymers are selected from the group consisting of carboxy methyl cellulose, a polyorthoester, pluronics, and a lactide-glycolide co-polymer.

9. The combination of claim 1, wherein the one or more polymers comprise one or more of methyl cellulose and carboxy methyl cellulose.

10. The combination of claim 1, wherein the one or more polymers comprise pluronic F-127.

11. The combination of claim 1, further comprising one or more permeation enhancers for enhancing permeation, diffusion, and sorption of the repellant composition into the seed.

12. The combination of claim 1, further comprising one or more plant nutrients.

13. The combination of claim 12, wherein the plant nutrients comprise one or more nutrients selected from the group consisting of a nitrogen source, a phosphorus source, a potassium source, calcium, magnesium, sulfur, iron, copper, boron, manganese, zinc, and molybdenum.

14. The combination of claim 1, further comprising fertilizer.

15. The combination of claim 1, further comprising one or more plant rooting hormones.

16. The combination of claim 1, wherein the one or more plant-derived, repellant chemicals comprise one or more alkaloids isolated from one or more members of the family Amaryllidaceae and the family Liliaceae.

17. The combination of claim 1, wherein the one or more plant-derived, repellant chemicals comprise one or more alkaloids isolated from one or more members of the genus *Narcissus*.

18. A combination comprising:
a plant seed containing suberin; and
a biopolymer system for treating seeds containing suberin, comprising:
one or more plant-derived repellant chemicals; and
one or more polymers, the polymers forming a matrix with the suberin and the plant-derived repellant chemicals to permit sustained release of the chemicals.

19. The combination of claim 1, wherein the one or more polymers comprise one or more natural, water-soluble polymers and resins selected from the group consisting of gums, starches, proteins, celluloses, agar, alginates, gelatin, pectin, soy bean, and tannins.

20. The combination of claim 1, wherein the one or more polymers comprise one or more synthetic, water-soluble polymers selected from the group consisting of polyvinyl alcohol, hydroxypropyl cellulose, maleic anhydride copolymers, polyacrylates, polyethylene glycols, polyvinyl pyrrolidone, hydroxyethyl cellulose, hydroxypropylmethylcellulose, cellulose ethers, polyquaternary amines, modified polyesters, sodium carboxymethyl cellulose, hydrogels, acrylamide co-polymers, polymeric surfactants, cationic polymers, and anionic/nonionic polymers.

21. A biopolymer system for treating plants, bulbs, or seeds containing suberin, comprising:

one or more plant-derived, repellant chemicals; and at least one polymer that is a pluronic polymer, the polymer forming a matrix with the suberin and the plant-derived, repellant chemicals to permit sustained release of the chemicals.

22. The biopolymer system of claim 21, wherein the at least one polymer is pluronic F-127.

23. A combination comprising a plant seed; and a composition comprising one or more plant-derived, repellant chemicals; and one or more polymers selected from bioerodible polymers and absorbable polymers, and a controlled release polymer, wherein the polymers form a matrix with the plant-derived, repellant chemicals to permit sustained release of the chemicals.

24. The combination of claim 23, wherein the one or more polymers are selected from the group consisting of carboxy methyl cellulose, a polyorthoester, pluronics, and a lactide-glycolide co-polymer.

25. The combination of claim 23, wherein the one or more polymers comprise pluronic F-127.

26. A combination comprising a plant seed; and a composition comprising one or more plant-derived, repellant chemicals; and one or more high molecular weight, hydrophilic polymers, wherein the polymers form a matrix with the plant-derived, repellant chemicals to permit sustained release of the chemicals.

27. The combination of claim 26, wherein the one or more polymers are selected from the group consisting of carboxy methyl cellulose, a polyorthoester, pluronics, and a lactide-glycolide co-polymer.

28. The combination of claim 26, wherein the one or more polymers comprise pluronic F-127.

29. A combination comprising a plant seed; and a composition comprising one or more plant-derived, repellant chemicals; and one or more high molecular weight, resorbable polymers, wherein the polymers form a hydrolytically and enzymatically degradable matrix with the plant-derived, repellant chemicals to permit sustained release of the chemicals.

30. The combination of claim 29, wherein the one or more polymers are selected from the group consisting of carboxy methyl cellulose, a polyorthoester, pluronics, and a lactide-glycolide co-polymer.

31. The combination of claim 29, wherein the one or more polymers comprise pluronic F-127.

32. A combination comprising a plant seed; and a composition comprising one or more plant-derived, repellant chemicals; and one or more hydrolytically and enzymatically degradable polymers wherein the polymers form a matrix with the plant-derived, repellant chemicals to permit sustained release of the chemicals.

33. The combination of claim 32, wherein the one or more polymers are selected from the group consisting of carboxy methyl cellulose, a polyorthoester, pluronics, and a lactide-glycolide co-polymer.

34. The combination of claim 32, wherein the one or more polymers comprise pluronic F-127.

* * * * *